(12) United States Patent
Cifter et al.

(10) Patent No.: US 9,095,515 B2
(45) Date of Patent: Aug. 4, 2015

(54) EZETIMIBE COMPOSITIONS

(75) Inventors: Umit Cifter, Istanbul (TR); Levent Oner, Ankara (TR); Ali Turkyilmaz, Istanbul (TR); Ibrahim Murat Uzer, Istanbul (TR); Gaye Ramazanoglu, Istanbul (TR)

(73) Assignee: Sanovel Ilac Sanayi Ve Ticaret Anonim Sirketi, Istanbul (TR)

( * ) Notice: Subject to any disclaimer, the term of this patent is extended or adjusted under 35 U.S.C. 154(b) by 876 days.

(21) Appl. No.: 12/723,808

(22) Filed: Mar. 15, 2010

(65) Prior Publication Data

US 2010/0234342 A1 Sep. 16, 2010

(30) Foreign Application Priority Data

Mar. 13, 2009 (TR) ............... a 2009 01961

(51) Int. Cl.
*A61K 31/397* (2006.01)
*A61K 9/20* (2006.01)

(52) U.S. Cl.
CPC .............. *A61K 9/2018* (2013.01); *A61K 31/397* (2013.01)

(58) Field of Classification Search
CPC .................. A61K 31/397; C07D 205/08
See application file for complete search history.

(56) References Cited

U.S. PATENT DOCUMENTS

2007/0275052 A1    11/2007   Mahjan et al.
2007/0275075 A1*   11/2007   Zalit et al. .................... 424/489

FOREIGN PATENT DOCUMENTS

| EP | 1849459 | 10/2007 |
|---|---|---|
| IN | 804MUM2004 | 3/2007 |
| WO | WO-2008101723 | 8/2008 |

OTHER PUBLICATIONS

European (IB) Search Report/Written Opinion for TR200901961, Dated Oct. 27, 2009 (9 pages).
A.R. Gennaro, Remington's Pharmaceutical Sciences, 18th edition, pp. 591, 1436-1437 (3 pages), (1990).
Handbook of Pharmaceutical Excipients, fifth edition, Rowe, Raymond C., Sheskey, Paul J., Owen Sian C., pp. 430-432 (3 pages), (2006).
Handbook of Pharmaceutical Excipients, fifth edition, Rowe, Raymond C., Sheskey, Paul J., Owen Sian C., pp. 705-707 (3 pages), (2006).

* cited by examiner

*Primary Examiner* — Wu-Cheng Winston Shen
*Assistant Examiner* — Christopher R Stone
(74) *Attorney, Agent, or Firm* — Kenyon & Kenyon LLP

(57) ABSTRACT

This invention is a novel pharmaceutical composition of ezetimibe or a pharmaceutically acceptable salt thereof comprising one or more pharmaceutically acceptable excipients having high bioavailability with improved solubility and dissolution rate which is stable throughout the shelflife, methods for their preparation, and methods for treatment using the same.

19 Claims, No Drawings

EZETIMIBE COMPOSITIONS

TECHNICAL ASPECT

This invention is a novel pharmaceutical composition of ezetimibe or a pharmaceutically acceptable salt thereof comprising one or more pharmaceutically acceptable excipients having high bioavailability with improved solubility and dissolution rate which is stable throughout the shelflife, methods for their preparation, and methods for treatment using the same.

More specifically, the novel pharmaceutical composition of ezetimibe is free of magnesium stearate and comprising micronized ezetimibe or a pharmaceutically acceptable salt thereof being in the form of particles having a median particle size of less than or equal to 2 μm. This novel pharmaceutical composition has a weight ratio of micronized ezetimibe to polyvinylpyrrolydone in the range of between 10:1 to 1:10 (w/w) and sodium stearyl fumarate to colloidal silicon dioxide in the range of between 10:1 to 1:10 (w/w).

BACKGROUND OF THE INVENTION

Ezetimibe is in a class of compounds known as lipid-lowering compounds that selectively inhibits the intestinal absorption of cholesterol and related phytosterols. Its chemical name is as (3R,4S)-1-(4-fluorophenyl)-3-[(3S)-3-(4-fluorophenyl)-3-hydroxypropyl]-4-(4-hydroxyphenyl)azetidin-2-one and has a chemical structure which is shown in the Formula 1.

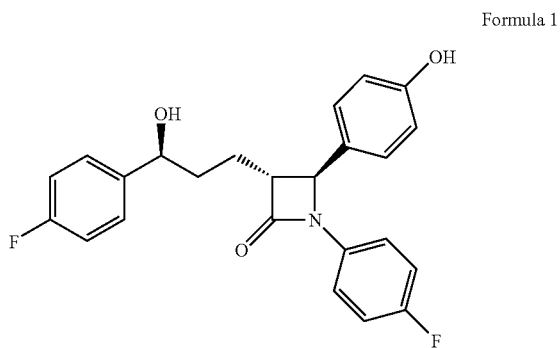 [SMILES: O=C1[C@H](CC[C@H](O)c2ccc(F)cc2)[C@@H](c2ccc(O)cc2)N1c1ccc(F)cc1]

Formula 1

Ezetimibe reduces blood cholesterol by inhibiting the absorption of cholesterol by the small intestine. Its mechanism of action differs from those of other classes of cholesterol-reducing compounds, such as HMG-CoA reductase inhibitors. It doesn't inhibit cholesterol synthesis in the liver, or increase bile acid excretion but inhibits the absorption of cholesterol, leading to a decrease in the delivery of intestinal cholesterol to the liver. Such mechanism is complementary to that of HMG-CoA reductase inhibitors.

Ezetimibe is marketed under the brand name ZETIA® or EZETROL®, which is available as a tablet for oral administration containing 10 mg of ezetimibe and the following inactive ingredients: croscarmellose sodium, lactose monohydrate, microcrystalline cellulose, povidone, sodium lauryl sulphate and magnesium stearate.

In prior art, there are many patents including ezetimibe in several different pharmaceutical compositions, for example ezetimibe is identified by the structural formula which is disclosed in EP patent, EP 0720599 B1 (Schering Corporation) 21.09.1993. Another EP patent EP 1353696 B1 (Schering Corporation) 26.01.2001 discloses the pharmaceutical formulation containing ezetimibe, lactose monohydrate, microcrystalline cellulose, povidone, croscarmellose sodium, sodium lauryl sulfate and magnesium stearate EP application, EP 1849459 A1 (Teva Pharmaceutical Ind. Ltd.) 06.03.2006, encompasses an ezetimibe composition comprising ezetimibe co-milled with at least one hydrophilic excipient such as saccharide or polysaccharide (e.g. starch). The ezetimibe composition further contains magnesium stearate, microcrystalline cellulose and povidone (page 6, ex. 2). Co-milled ezetimibe has a particle size d (0.5) less than or equal to about 5 μm and d(0.9) less than or equal to about 20 μm, (page 3, paragraph 22). In this invention, about 40% to about 70% ezetimibe composition is dissolved in 20 minutes, and about 50% or more of the ezetimibe composition is dissolved in 40 minutes, (page 3, paragraph 21).

US application US 2007/0275052 A1 (Glenmark Pharmaceuticals Ltd.) 24.05.2006, also discloses the pharmaceutical composition comprising micronized ezetimibe of which about 90% of the particles are not more than about 7 microns and of which about 50% of the particles are not more than about 4 microns (page 1-2, paragraph 18). In this invention one of the pharmaceutical formulations contains ezetimibe, lactose monohydrate, crospovidone, povidone and magnesium stearate (page 2, ex. 1) and other pharmaceutical formulation contains ezetimibe, lactose monohydrate, sodium starch glycolate, sodium lauryl sulphate, povidone and magnesium stearate (page 2, ex. 2). PCT application WO 2008/101723 A2 (Krka) 23.02.2007, relates to a pharmaceutical composition comprising at least one cholesterol absorbtion inhibitor such as ezetimibe in amorphous form and at least one hydrophilic polymer.

Ezetimibe is reported as practically insoluble in water, which cause it to exhibit a low dissolution rate in aqueous media such as gastrointestinal fluids, which can result in low bioavailability after oral ingestion.

In prior art, it is known that for improving bioavailability, particle size reduction is used for water-insoluble drugs. However, particle size reduction is not always effective enough for increasing the dissolution rate of a drug to a certain required value. Many water-insoluble drugs have a strong tendency to agglomerate into larger particles with an overall decrease in effective surface area during the manufacturing process. Further it has been reported that extremely small sizes (less than 10 μm) may be inadvisable for some drug substances. (A. R. Gennaro, Remington's Pharmaceutical Sciences, 18$^{th}$ ed., pages 591, 1436-1437). The technical problem of particle size reduction may occur during the manufacturing and tabletting procedure such as agglomeration and bad flowabilty because of having less glidant and lubricant characteristics of drug substances in powder form.

As shown above many different approaches how to improve bioavailability of low soluble drugs have been disclosed in the prior art. Therefore, there is a need in the art to provide improved pharmaceutical compositions of ezetimibe that overcome the problems of the prior art with having high bioavailability with improved solubility and dissolution rate which is stable throughout the shelflife, commercially cost low and plant-friendly manufacturing process.

DESCRIPTION OF THE INVENTION

This invention is a novel pharmaceutical composition of ezetimibe or a pharmaceutically acceptable salt thereof, comprising one or more pharmaceutically acceptable excipients having high bioavailability with improved solubility and dissolution rate which is stable throughout the shelflife, methods for their preparation, and methods for treatment using the same.

The novel pharmaceutical composition of this invention is free of magnesium stearate and comprising micronized ezetimibe or a pharmaceutically acceptable salt thereof being in the form of particles having a median particle size of less than or equal to 2 µm. It has now found that ezetimibe having a very small median particle size can not be easily formulated into solid pharmaceutical compositions if it has a narrow particle size distrubition.

As used here in, "particle size distribution" means the cumulative volume size distrubution as tested by any conventionally accepted method such as the laser diffraction method. "median particle size" means, d(0.5), the size at which 50% by volume of the particles are finer and "d (0.9)" means that the size at which %90 by volume of the particles are finer.

In prior art, for improving dissolution, particle size reduction is used for water-insoluble drugs. However, particle size reduction is not always effective enough for increasing the dissolution rate of a drug to a certain required value. Many water-insoluble drugs have a strong tendency to agglomerate during the manufacturing process into larger particles with an overall decrease in effective surface area. The technical problem of particle size reduction may occur during the manufacturing and tabletting procedure such as agglomeration and bad flowabilty because of having less glidant and lubricant characteristics of powders or granules. Further, flow properties of drugs can be influenced by particle size, and particle size reduction to extremely small sizes (less than 10 µm) may be inadvisable for some drug substances. Such effects act as dissolution rate limiting steps since they minimize maximum drug surface-liquid contact.

It is known that, pressing granules or powders into tablet form which have the median particle size less than about 2 µm is very difficult. This pharmaceutical composition according to the invention overcomes the problem arising from the prior art by providing a magnesium stearate free pharmaceutical composition of ezetimibe which overcomes the sticking problem of the powder or granules into punches in tablet press machine during the manufacturing and tabletting process by the help of using the sodium stearyl fumarate and colloidal silicon dioxide in a weight ratio of between 10:1 to 1:10 (w/w), and using micronized ezetimibe and polyvinylpyrrolydone in a weight ratio of between 10:1 to 1:10 (w/w). This pharmaceutical composition of the present invention has also high bioavailability with improved solubility and dissolution rate which is stable throughout the shelflife.

One of the preferred embodiments of this invention is directed to narrow particle size distrubition of micronized ezetimibe composition wherein the ratio between the median particle size and d (0.9) is equal to or greater than 0.30. Preferably, the ratio between the median particle size and d (0.9) is between 0.35 and 0.60, more preferably it is 0.40 and 0.50.

In one embodiment, the pharmaceutical composition of this invention comprises micronized ezetimibe particles having a median particle size of less than or equal to about 2 µm. In another embodiment, the pharmaceutical composition of this invention comprises micronized ezetimibe particles having a d (0.9) less than or equal to about 4.5 µm.

One of the main object of the present invention is a novel pharmaceutical composition of ezetimibe or a pharmaceutically acceptable salt thereof which is free of magnesium stearate.

It is known that magnesium stearate has some disadvantages despite being a good lubricant and because of this it is used in small quantities during drug manufacturing process. Magnesium stearate is practically insoluble in water and because of this hydrophobic characteristic it may retard the dissolution of a drug from a solid dosage form such as tablet or capsule. Tablet and especially capsule dissolution is sensitive to both the amount of magnesium stearate in the formulation and the blending time. Blending time should be limited. Long blending times can result in the formulation of hydrophobic powder beds that do not disperse easily and overblending can cause compaction problems. Tablet dissolution rate and crushing strength decreased as the time of blending increased; and magnesium stearate may also increase tablet friability. Blending times with magnesium stearate should therefore be carefully controlled. (Handbook of Pharmaceutical Excipients, fifth edition, Rowe, Raymond C., Sheskey, Paul J., Owen, Sian C., pages 430-432).

Sodium stearyl fumarate is extremely effective lubricant and less hydrophobic than magnesium stearate and has a less retardant effect on tablet dissolution than magnesium stearate. Sodium stearyl fumarate also doesn't have the over blending problems seen with magnesium steare. (Handbook of Pharmaceutical Excipients, fifth edition, Rowe, Raymond C., Sheskey, Paul J., Owen, Sian C., pages 705-707).

In this pharmaceutical composition of the present invention, it is objected to use sodium stearyl fumarate in combination with colloidal silicon dioxide instead of magnesium stearate as a lubricant and glidant to overcome the technical problems which are shown above.

The present invention is further directed to use colloidal silicon dioxide as a glidant and surprisingly we have found that in a specific weight ratio in combination with sodium stearyl fumarate it has a synergistic effect over the dissolution rate and glidant characteristic of colloidal silicon dioxide is increased. This also increased the manufacturing process quality in solid dosage forms. The preferred specific weight ratio of sodium stearyl fumarate to colloidal silicon dioxide is 10:1 to 1:10 (w/w). Preferably, the weight ratio of sodium stearyl fumarate to colloidal silicon dioxide is 7:1 to 1:1 (w/w), more preferably it is 5:1 to 3:1 (w/w).

Another embodiment of the present invention is using the polyvinylpyrrolydone with micronized ezetimibe which is finely distributed within to obtain a hydrophilic surface to increase its solubility and to prevent agglomeration which can occur during hydrophilization of hydrophobic micronized ezetimibe surface, among the hydrophobic micronized ezetimibe particules of the pharmaceutical composition. Heretofore, there has been no recognition in the prior art of the synergistic effect of polyvinylpyrrolydone on increasing the solubility of micronized ezetimibe in a preferred weight ratio. Surprisingly it has been found that when the weight ratio of polyvinylpyrrolydone to ezetimibe is between 10:1 to 1:10 (w/w), preferably, 5:1 to 1:1 (w/w), more preferably when it is 3:1 to 2:1 (w/w) the solubility of ezetimibe is increased.

In this present application we claim that without using magnesium stearate in the pharmaceutical composition of ezetimibe which has a narrow particle size distrubiton, we reached a better dissolution rate, 85% or more of the ezetimibe dissolves in 15 min. (shown in Table 1). Further, addition of sodium stearyl fumarate and colloidal silicon dioxide in a specific weight ratio which is 5:1 to 3:1 (w/w) and addition of ezetimibe and polyvinylpyrrolydone in a specific ratio which is 3:1 to 2:1 (w/w) also improves the dissolution rate.

Preferred pharmaceutical composition of the present invention is consisting of;
- 1 to 20% ezetimibe
- 20 to 60% microcrystalline cellulose
- 15 to 60% lactose monohydrate
- 1 to 20% polyvinylpyrrolydone
- 1 to 20% croscarmellose sodium
- 0.1 to 5% sodium lauryl sulfate
- 0.1 to 5% colloidal silicon dioxide
- 0.1 to 5% sodium stearyl fumarate The pharmaceutical compositions of the invention include such as powders, sachets, tablets, capsules, solutions etc. The preparation of pharmaceutical forms of this kind is well-known per se from the prior art.

Preferably, pharmaceutical compositions of this present invention are directed to tablets. A process of making pharmaceutical compositions for tabletting can be direct compression, wet granulation or dry granulation which are commonly known in prior art.

The pharmaceutical compositions according to the present invention may further comprise one or more other active ingredients such as other lipid lowering drugs for example fenofibrate, HMG-CoA reductase inhibitors such as representatives of statin group for example atorvastatin, rosuvastatin, simvastatin or salts thereof and any mixtures thereof.

The pharmaceutical compositions of the present invention further comprise one or more pharmaceutically acceptable excipients. Suitable pharmaceutically acceptable excipients include, but are not limited to, diluents, binders, disintegrants, surface active agents, glidants, lubricants and the like and mixtures thereof.

Suitable diluents may include but not limited to lactose, microcrystalline cellulose, starch, mannitol, glucose and/or mixtures thereof. Most preferred diluents are lactose and microcrystalline cellulose.

Suitable binders may include but not limited to polyvinylpyrrolidone (povidone), cellulose derivatives such as hydroxypropyl methyl cellulose (HPMC), hydroxypropyl cellulose (HPC), carboxy methyl cellulose (CMC), methyl cellulose (MC) and the like and mixtures thereof. Most preferred binder is polyvinylpyrrolidone.

Suitable disintegrants may include but not limited to crosscarmellose sodium, sodium starch glycolate, crospovidone, starch (e.g., corn, potato) and the like and mixtures thereof. Most preferred disintegrant is crosscarmellose sodium.

Suitable surface active agents may include but not limited to sodium lauryl sulphate, polyoxyethylene glycol esters, sulphate containing surfactants and the like and mixtures thereof. Most preferred one is sodium lauryl sulphate.

Suitable glidants may include but not limited to colloidal silicon dioxide, talc, aluminium silicate and the like and mixtures thereof. Most preferred glidant of this invention is colloidal silicon dioxide.

Suitable lubricants are sodium stearyl fumarate, talc, polyethylene glycol, stearic acid and the like and mixtures thereof. Most preferred lubricant of this invention is sodium stearyl fumarate.

Another aspect of the present invention is the manufacturing process of the pharmaceutical compositions of ezetimibe according to the present invention. The pharmaceutical compositions of ezetimibe of the present invention can be prepared in a fast, efficient, commercially cost low and plant-friendly manufacturing process.

The manufacturing process for the preparation of the pharmaceutical composition of ezetimibe comprising the steps;
a. admixing of ezetimibe with polyvinylpyrrolydone and with one or more pharmaceutical excipients,
b. forming a wet granulation mixture,
c. drying the granules,
d. sieving the dried granules
e. blending the granules with colloidal silicon dioxide and sodium stearyl fumarate and with one or more excipients
f. compressing the granules into tablet form The pharmaceutical composition according to the present invention further comprise one or more other active ingredients; these ingredients can be added in any step of the manufacturing process as described above.

In one of the preferred embodiments of this invention the pharmaceutical composition of this present invention have a long-term shelf-life of 24 months or more at ambient temperature, in its original packaging.

The pharmaceutical compositions of the present invention may be formulated for administration to mammals such as humans or animals for treating different lipid disorders such as primary hypercholesterolemia or homozygous sitosterolemia.

This invention is further defined by reference to the following examples. In the following examples micronized ezetimibe has the ratio between the median particle size and d(0.9) is about 0.45. Although the example is not intended to limit the scope of the present invention, it should be considered in the light of the description detailed above. It will be apparent to those skilled in the art that many modifications, both to materials and methods, may be practiced without departing from the scope of the invention.

EXAMPLE 1

Pharmaceutical Composition of Ezetime (Particle Size of d(0.9)=4.10 µm and Median Particle Size d(0.5)=1.85 µm)

| Ingredients | Amount (mg/tablet) |
|---|---|
| Ezetimibe | 10 |
| Microcrystalline cellulose | 27.7 |
| Lactose monohydrate | 44.45 |
| Polyvinylpyrrolydone | 4.25 |
| Crosscarmellose sodium | 10 |
| Sodium Lauryl sulfate | 2 |
| Colloidal silicon dioxide | 0.3 |
| Sodium stearyl fumarate | 1.3 |

EXAMPLE 2

| Ingredients | Amount (mg/tablet) |
|---|---|
| Ezetimibe | 10 |
| Microcrystalline cellulose | 50 |
| Lactose monohydrate | 22.15 |
| Polyvinylpyrrolydone | 4.25 |
| Crosscarmellose sodium | 10 |
| Sodium Lauryl sulfate | 2 |
| Colloidal silicon dioxide | 0.3 |
| Sodium stearyl fumarate | 1.3 |

EXAMPLE 3

| Ingredients | Amount (mg/tablet) |
| --- | --- |
| Ezetimibe | 10 |
| Microcrystalline cellulose | 28 |
| Lactose monohydrate | 38.7 |
| Polyvinylpyrrolydone | 10 |
| Crosscarmellose sodium | 10 |
| Sodium Lauryl sulfate | 2 |
| Colloidal silicon dioxide | 0.3 |
| Sodium stearyl fumarate | 1.0 |

EXAMPLE 4

The pharmaceutical composition of this present invention was tested for its dissolution profile against the ezetimibe composition including magnesium stearate in 500 ml of 0.05M acetate buffer at pH 4.5 containing 0.45 sodium lauryl sulphate at 37° C. using a USP paddle method rotating at 50 RPM. Results are shown in Table 1.

TABLE 1

| Time (min) | Mg stearate free (%) | including Mg stearate (%) |
| --- | --- | --- |
| 0 | 0.0 | 0.0 |
| 5 | 47.1 | 65.9 |
| 10 | 59.6 | 86.6 |
| 15 | 80.6 | 92.4 |

The pharmaceutical composition of example 4 which is used against for dissolution test, is comprising the same amounts of example 1 but including magnesium stearate instead of sodium stearyl fumarate and colloidal silicon dioxide.

The invention claimed is:

1. A pharmaceutical composition comprising
   (a). micronized ezetimibe or a pharmaceutically acceptable salt thereof being in the form of particles having a median particle size of less than or equal to 2 μm,
   (b). polyvinylpyrrolydone wherein micronized ezetimibe is finely distributed within the weight ratio of micronized ezetimibe to polyvinylpyrrolydone in the range of between 5:1 to 1:1 (w/w), and
   (c). sodium stearyl fumarate and colloidal silicon dioxide wherein the weight ratio of sodium stearyl fumarate to colloidal silicon dioxide is in the range of between 7:1 to 1:1 (w/w), and wherein said composition is free of magnesium stearate.

2. The pharmaceutical composition of claim 1, wherein micronized ezetimibe has a ratio between the median particle size and d(0.9) which is equal to or greater than 0.30.

3. The pharmaceutical composition of claim 1, wherein micronized ezetimibe has a ratio between the median particle size and d(0.9) which is between 0.35 and 0.60.

4. The pharmaceutical composition of claim 1, wherein micronized ezetimibe has a ratio between the median particle size and d(0.9) which is between 0.40 and 0.50.

5. The pharmaceutical composition of claim 1, wherein the micronized ezetimibe has a d(0.9) less than or equal to 4.5 μm.

6. The pharmaceutical composition of claim 1, wherein the weight ratio of micronized ezetimibe to polyvinylpyrrolydone is in the range of between 3:1 to 2:1 (w/w).

7. The pharmaceutical composition of claim 1, wherein the weight ratio of sodium stearyl fumarate to colloidal silicon dioxide is in the range of between 5:1 to 3:1 (w/w).

8. The pharmaceutical composition of claim 1, further comprising at least one excipient selected from the group of diluents, disintegrants, surface active agents, binders, lubricants, glidants and mixtures thereof.

9. The pharmaceutical composition of claim 8, wherein the diluent is selected from lactose, microcrystalline cellulose, starch, mannitol, glucose and mixtures thereof.

10. The pharmaceutical composition of claim 8, wherein the disintegrant is selected from crosscarmellose sodium, sodium starch glycolate, crospovidone, starch and mixtures thereof.

11. The pharmaceutical composition of claim 8, wherein the surface active agent is selected from sodium lauryl sulphate, polyoxyethylene glycol esters, sulphate containing surfactants and mixtures thereof.

12. The pharmaceutical composition of claim 8, wherein the binder is selected from polyvinylpyrrolidone, cellulose derivatives such as hydroxypropyl methyl cellulose, hydroxypropyl cellulose, carboxy methyl cellulose, methyl cellulose and mixtures thereof.

13. The pharmaceutical composition of claim 8, wherein the lubricant is selected from sodium stearyl fumarate, talc, polyethylene glycol, stearic acid and mixtures thereof.

14. The pharmaceutical composition of claim 8, wherein the glidant is selected from colloidal silicon dioxide, talc, aluminium silicate and mixtures thereof.

15. The pharmaceutical composition of claim 1, consisting of
   (a). 1 to 20% ezetimibe,
   (b). 20 to 60% microcrystalline cellulose,
   (c). 15 to 60% lactose monohydrate,
   (d). 1 to 20% polyvinylpyrrolydone,
   (e). 1 to 20% crosscarmellose sodium,
   (f). 0.1 to 5% sodium lauryl sulfate,
   (g). 0.1 to 5% colloidal silicon dioxide, and
   (h). 0.1 to 5% sodium stearyl fumarate.

16. The pharmaceutical composition of claim 1, in the form of a powder, sachet, tablet or a capsule.

17. The pharmaceutical composition according to claim 1, in the form of a tablet.

18. The pharmaceutical composition of claim 1, wherein 85% or more of the ezetimibe is dissolved in 15 min in 500 ml of 0.05M acetate buffer at pH 4.5 containing 0.45% sodium lauryl sulfate at 37° C. using a USP paddle method rotating at 50 RPM.

19. A process for the preparation of the pharmaceutical composition of claim 1, comprising the steps of:
   (a). admixing of ezetimibe with polyvinylpyrrolydone and with one or more pharmaceutical excipients;
   (b). forming a wet granulation mixture;
   (c). drying the granules;
   (d). sieving the dried granules;
   (e). blending the granules with colloidal silicon dioxide and sodium stearyl fumarate and with one or more excipients; and
   (f). compressing the granules into tablet form.

* * * * *